United States Patent [19]

Myers

[11] Patent Number: 4,682,597
[45] Date of Patent: Jul. 28, 1987

[54] SCLERAL DISSECTOR

[76] Inventor: William D. Myers, 5855 Wingcroft Ct., Birmingham, Mich. 48010

[21] Appl. No.: 754,943

[22] Filed: Jul. 15, 1985

[51] Int. Cl.⁴ .............................................. A61F 17/32
[52] U.S. Cl. ...................................... 128/305; 604/22; 30/289
[58] Field of Search ............... 128/305, 310, 314, 317; 30/294, 286, 287, 293, 320, 353

[56] References Cited
FOREIGN PATENT DOCUMENTS 800690 11/1950 Fed. Rep. of Germany ...... 128/305
85/01431 5/1983 PCT Int'l Appl. ................ 128/305

Primary Examiner—Henry A. Bennet
Attorney, Agent, or Firm—Gifford, Groh, VanOphem, Sheridan, Sprinkle & Dolgorukov

[57] ABSTRACT

The present invention provides a scleral dissector for use in implanting artificial lens in human eyes. The dissector includes an elongated handle having a substantially planar cutting blade secured to and extending laterally outwardly from one end. A substantially planar guide is also attached to the handle so that the guide is spaced from and generally parallel to the blade. The guide is adapted to abut against the outer surface of the sclera during a scleral dissection. The spacing between the guide and the blade is preferably adjustable.

6 Claims, 4 Drawing Figures

SCLERAL DISSECTOR

BACKGROUND OF THE INVENTION

I. Field of the Invention

The present invention relates generally to medical instruments and, more particularly, to a scleral dissector.

II. Description of the Prior Art

Following extracapsular surgery, an artificial lens is frequently implanted into the eyeball in order to restore normal, or near normal, vision to the patient. The lens can be implanted either into the anterior chamber, iris or posterior chamber of the eyeball although the modern trend is toward posterior chamber lens implants.

In order to implant the artificial lens, an incision is made through the eyeball and the artificial lens is inserted through the incision and implanted at the desired position in the eyeball. The incision is then sutured and allowed to heal.

Previously, the incision in the eyeball has been made at the junction between the cornea and the sclera which provided direct access to both the anterior and posterior chambers as well as the iris. One disadvantage of this procedure, however, is that after the incision has been sutured, the patient suffers from very severe stigmatism resulting from distortion of the cornea at the point of the incision. Such stigmatism oftentimes lasts for a period of months and then vanishes but, in other cases, the stigmatism is permanent.

With reference to prior art FIG. 1, in order to avoid stigmatism following the lens implantation, many surgeons now make a radially extending incision 10 through the sclera 12 at a position radially spaced from the cornea 14 so that the incision extends only partway through the sclera 12. A prior art scleral dissector 16 having an elongated handle 18 with a cutting blade 20 extending laterally outwardly from one end is then inserted into the incision 10 and used to make a tangentially extending incision through the sclera 12 and towards the cornea 14. In doing so, the scleral dissector 16 forms a flap 24 in the sclera 12. This flap 24 is then lifted to complete an incision through the sclera 12 and through which the artificial lens is inserted and implanted in place.

While the above described procedure effectively eliminates the problem of severe stigmatism following the lens implantation, great care must be exercised by the surgeon in cutting the flap 24 since the sclera 12 is very thin walled. Thus, if the dissector 16 is tilted as shown in exaggeration by the dashed and dotted line at 16' in FIG. 1, the blade 20 will cut through the outer surface of the sclera 12 and destroy the flap 24. Conversely, if the dissector is tilted as shown in exaggeration by the dashed line at 16", the blade 20 can cut through the inner surface of the sclera 12 at a position radially spaced from the cornea 14. In either event, extensive repair of the eyeball is required.

SUMMARY OF THE PRESENT INVENTION

The present invention provides a scleral dissector which overcomes all of the above mentioned disadvantages of the previously known dissectors.

In brief, the scleral dissector of the present invention comprises an elongated handle having a substantially planar cutting blade secured to and extending laterally outwardly from one end. The handle is slidably positioned through an elongated guide tube having a generally planar guide extending laterally outwardly from one end so that the guide and the cutting blade are spaced part but generally parallel to each other. An adjustment knob at the opposite end of the guide tube and the handle enables adjustment of the relative longitudinal position between the handle and the guide tube and thus varies the space in between the guide and the cutting blade.

In practice, the space in between the guide and the cutting blade is adjusted to substantially one half the thickness of the patient's sclera and the cutting blade is inserted through an incision in the eye and so that the guide abuts the outer surface of the sclera. By maintaining the guide in abutment with the outer surface of the sclera the surgeon forms the flap on the sclera adjacent the cornea without fear of cutting through either the interior or exterior surface of the sclera.

BRIEF DESCRIPTION OF THE DRAWING

A better understanding of the present invention will be had upon reference to the following detailed description when read in conjunction with the accompanying drawing wherein like reference characters refer to like parts throughout the several views and in which.

DETAILED DESCRIPTION OF THE PRESENT INVENTION

Figure 1:
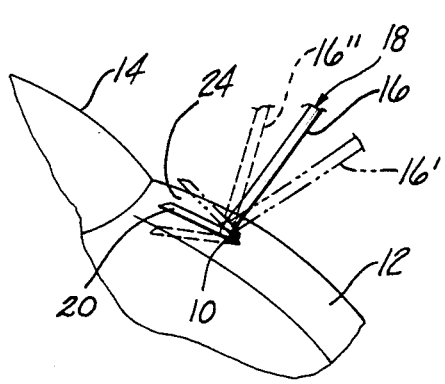
FIG. 1 is a prior art figure.
Figure 2:
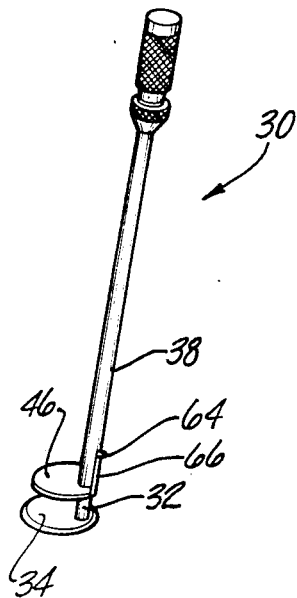
FIG. 2 is a pespective view illustrating a preferred embodiment of the present invention.
Figure 3:
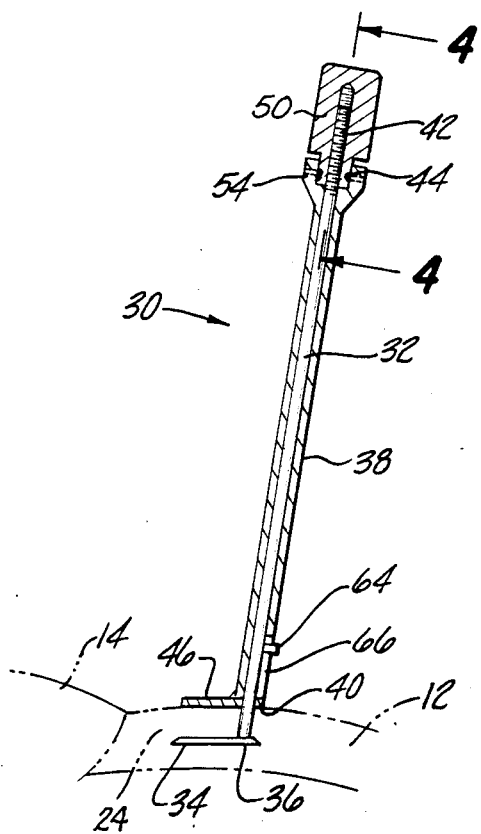
FIG. 3 is a longitudinal sectional view of the preferred embodiment of the present invention.

With reference first to FIGS. 2 and 3, a preferred embodiment of the scleral dissector 30 of the present invention is thereshown and comprises an elongated handle 32 which is generally cylindrical in cross sectional shape. A cutting blade 34 extends laterally outwardly from one end 36 of the handle 32 and, in the conventional fashion, includes a cutting edge around its entire periphery.

Figure 4:
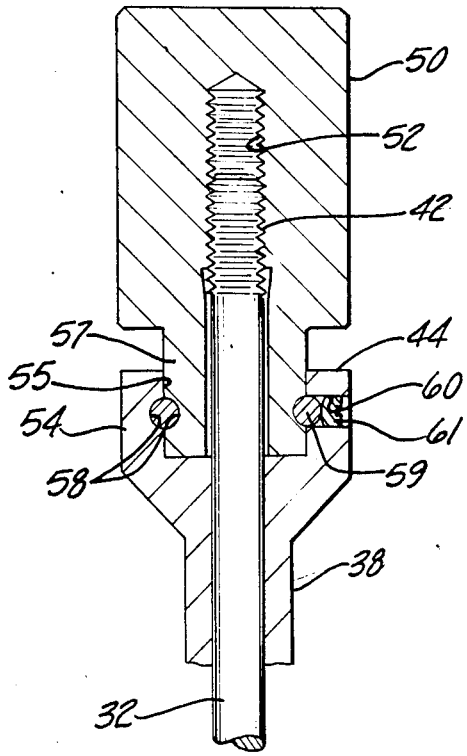
FIG. 4 is a fragmentary sectional view of a portion of the preferred embodiment of the present invention and enlarged for clarity.

Referring now to FIGS. 2–4, the handle 32 is longitudinally slidably positioned through an elongated guide tube 38 so that the lower end 36 of the handle 32 protrudes outwardly from a lower end 40 of the guide tube and, similarly, an upper end 42 of the handle 32 protrudes upwardly from an upper end 44 of the guide tube 38. As best shown in FIGS. 2 and 3, a generally planar guide 46 is secured to and extends laterally outwardly from the lower end 40 of the guide tube 38 so that the guide 46 is substantially parallel to, but spaced apart from, the cutting blade 34.

With reference now to FIGS. 3 and 4, the scleral dissector of the present invention preferably includes means for adjusting the relative longitudinal position between the guide tube 38 and the handle 32 and thus for adjusting the spacing between the blade 34 and the guide 46. In a preferred form of the invention, this adjustment means comprises a cylindrical knob 50 having an internally threaded axial bore 52. In addition, the upper end 42 of the handle 32 is externally threaded and threadably cooperates with the threaded bore 52 so that rotation of the knob 50 relative to the handle 32 axially displaces the handle 32 with respect to the knob 50.

As best shown in FIG. 4, the guide tube 38 includes a radially outwardly extending flange 54 at its upper end 44. An enlarged diameter axial bore 55 is formed at the upper end 44 of the flange 54 while a reduced diameter portion 57 of the knob 50 is rotatably received within the bore 55.

In order to prevent axial movement between the knob 50 and the guide tube 38, facing ball bearing races 58 are formed in the bore 55 and the reduced diameter portion 57 of the knob 50. Ball bearings 59 are then inserted through an access opening 60 in the flange 54 and between the races 58 and the access opening 60 is then closed by a set screw 61. The ball bearings 59 thus allow the knob 50 to freely rotate with respect to the guide tube 38 but simultaneously prevent axial movement.

In order to prevent relative rotation between the handle 32 and the guide tube 38, the handle 32 preferably includes a pin 64 (FIGS. 2 and 3) extending radially outwardly from the handle 32 adjacent its lower end 36. This pin 64 is slidably received within a slot 66 at and open to the lower end 40 of the guide tube 38. The pin 64 and slot 66 arrangement permits longitudinal movement between the handle 32 and the guide tube 38 but prevents relative rotation between the guide tube 38 and handle 32.

Since the guide tube 38 and handle 32 are fixed against rotation relative to each other by a pin 64 and slot 66, rotation of the knob 50 relative to the guide tube 38 axially displaces the handle 32 relative to the guide tube 38 due to the threaded engagement between the handle end 52 and the knob threaded bore 52. Rotation in one direction reduces the spacing between the guide 46 and blade 34 while, conversely, rotation in the other direction increases the spacing.

It will be understood, of course, that other means may be employed to adjust the spacing between the guide 46 and the blade 34 without deviation from the spirit of the invention. Furthermore, as will become shortly apparent, a total adjustment range of only a few millimeters between the guide 46 and blade 34 is desirable.

With reference now to FIG. 3, the depth or thickness of the flap 24 in the sclera 12 is first determined in any conventional fashion and the knob 50 is then adjusted until the spacing between the guide 46 and blade 34 equals the desired thickness of the flap 24. This spacing is typically about one half the thickness of the sclera 12.

The blade 34 is then inserted into the sclera 12 into the position shown in FIG. 3 so that the guide 46 abuts against the outer surface of the sclera 12. The surgeon then cuts the flap 24 by moving the dissector 30 in a lateral motion while keeping the guide 46 flatly against the outer surface of the sclera 12. Since the guide 46 is parallel to the blade 34, the chance of cutting through either the interior or exterior surface of the sclera 12 is completely avoided.

Replacement of the cutting blade 34 together with the handle 32, is easily accomplished by simply rotating the knob 50 until the threaded end 42 of the handle 32 disengages from the threaded knob bore 52 and then sliding the handle 32 out from the guide tube 38. A new blade 34 together with this handle 32 is then inserted through the guide tube 38 and the knob 50 rotated until the proper spacing between the guide 46 and blade 34 is obtained.

Although in the preferred form of the invention, the spacing between the guide 46 and blade 34 is adjustable, the guide 46 can be alternatively secured to the handle 32 at a fixed position so that the spacing between the guide 46 and blade 34 is fixed. In this event, however, it will be desireable to have a set of dissectors with different spacings between the guide 46 and blade 34 in order to accomodate different eyeballs with different scleral thicknesses.

From the foregoing, it can be seen that the present invention provides a scleral dissector for artifical lens implantation which is not only simple in construction but effective in use. Furthermore, the dissector of the present invention entirely eliminates the possibility of inadvertantly cutting through the interior or exterior surface of the sclera.

Having described my invention, however, many modifications thereto will become apparent to those skilled in the art to which it pertains without deviation from the spirit of the invention as defined by the scope of the appended claims.

I claim:

1. A scleral dissector comprising:
an elongated handle,
a substantially planar cutting blade secured to and extending laterally outwardly from one end of the handle,
a substantially planar guide,
means for attaching said guide to said handle so that said guide is spaced from said blade and so that said guide and said blade both lie in planes which are substantially parallel to each other and transverse with respect to the axis of the handle, said guide having a surface facing the blade which is adapted to abut against the outer surface of the sclera of an eyeball during a scleral dissection.

2. The invention as defined in claim 1 and comprising means for adjusting the spacing between said blade and said guide.

3. The invention as defined in claim 2 and comprising an elongated guide tube, said guide extending laterally outwardly from one end of said guide tube, said handle slidably extending through said guide tube, said adjusting means comprising means for varying the relative longitudinal position of said handle with respect to said guide tube.

4. The invention as defined in claim 3 wherein said handle includes a threaded portion at its other end and wherein said varying means comprises a knob having an internally threaded bore which threadably engages said threaded handle end, and means for securing said knob to said guide tube to permit rotation between said knob and said guide tube and simultaneously to prevent longitudinal movement between said knob and said guide tube.

5. The invention as defined in claim 4 and comprising means for preventing rotational movement between said guide tube and said handle.

6. The invention as defined in claim 4 wherein said means for securing said guide tube to said knob comprises facing ball bearing races on said guide tube and said knob, and ball bearings between said races.

* * * * *

UNITED STATES PATENT AND TRADEMARK OFFICE
CERTIFICATE OF CORRECTION

PATENT NO. : 4,682,597

DATED : July 28, 1987

INVENTOR(S) : William D. Myers

It is certified that error appears in the above-identified patent and that said Letters Patent is hereby corrected as shown below:

Col. 1, line 32, delete "implanation" and insert --implantation--.

Col. 2, line 3, delete "part" and insert --apart--.

Col. 2, line 27, delete "pespective" and insert --perspective--.

Col. 3, line 32, delete "52", first occurrence, and insert --42--.

Col. 4, line 10, delete "accomodate" and insert --accommodate--.

Signed and Sealed this

Fifth Day of January, 1988

Attest:

DONALD J. QUIGG

Attesting Officer

Commissioner of Patents and Trademarks